US007737180B2

(12) United States Patent
Makovec et al.

(10) Patent No.: US 7,737,180 B2
(45) Date of Patent: Jun. 15, 2010

(54) USE OF NEBOGLAMINE (CR 2249) AS AN ANTIPSYCHOTIC AND NEUROPROTECTIVE

(75) Inventors: Francesco Makovec, Lesmo (IT); Lucio Claudio Rovati, Monza (IT)

(73) Assignee: Rottapharm S.p.A., Milan (IT)

( * ) Notice: Subject to any disclaimer, the term of this patent is extended or adjusted under 35 U.S.C. 154(b) by 476 days.

(21) Appl. No.: 11/569,545

(22) PCT Filed: May 23, 2005

(86) PCT No.: PCT/EP2005/052340

§ 371 (c)(1),
(2), (4) Date: Nov. 22, 2006

(87) PCT Pub. No.: WO2005/115373

PCT Pub. Date: Dec. 8, 2005

(65) Prior Publication Data

US 2007/0249715 A1    Oct. 25, 2007

(30) Foreign Application Priority Data

May 24, 2004    (IT)    ........................ TO2004A0343

(51) Int. Cl.
*A61K 31/195*    (2006.01)
(52) U.S. Cl. .................................................... 514/561
(58) Field of Classification Search ................... 514/561
See application file for complete search history.

(56) References Cited

U.S. PATENT DOCUMENTS 3,665,037 A * 5/1972 Murakami et al. .......... 564/300

FOREIGN PATENT DOCUMENTS

WO    WO 9420454    9/1994

WO    WO 03045913    5/2003

OTHER PUBLICATIONS

Flint et al. A qualitative analysis of the negative symptoms of schizophrenia interfering with academic and social success, and the exacerbators and diminishers of those symptoms. Dissertation Abstracts International, 2003 vol. 64, No. 12A. p. 4420. Abstract.*
Garofalo et al. CR 2249: a New putative memory enhnacer. Behavioural studies on learning and memory in rats and mice. J. Pharm. Pharmacol. 1996, 48, pp. 1290-1297.*
Victor Peralta, Are There More Than Two Syndromes in Schizophrenia? A Critique of the Positive-Negative Dichotomy, British Journal of Psychiatry (1992), 161, 335-343.
R.D. Porsolt, Behavioural Despair in Mice: A Primary Screening Test for Antidepressants, Arch. int. Pharmacodyn. 229, 327-336 (1977).
N. R. Swerdlow, Effects of Spiperone, Raclopride, SCH 23390 and Clozapine on Apomorphine Inhibition of Sensorimotor Gating of the Startle Response in the Rat, The Journal of Pharmacology and Experimental Therapeutics, vol. 256, No. 2, U.S.
J. David Jentsch, The Neuropsychopharmacology of Phencyclidine: From NMDA Receptor Hypofunction to the Dopamine Hypothesis of Schizophrenia, Neurospychopharmacology, 1999-vol. 20, No. 3.
Paolo Garofalo, CR 2249: a New Putative Memory Enhancer. Behavioural Studies on Learning and Memory in Rats and Mice, J. Pharm. Pharmacol. 1996, 48: 1290-1297, Feb. 27, 1996.
M. Lanza, Characteriztion of a Novel Putative Cognition Enhancer Mediting Facilittion of Glycine Effect on Strychnine-Resistant Sites Coupled to NMDA Receptor Complex, Neuropharmacology, vol. 26, No. 8, pp. 1057-1064, 1997.
Yousry Sayed, The Dopamine Hypothesis of Schizophrenia and the Antagonistic Action of Neuoleptic Drugs—A Review; The British Library, vol. 19, No. 2, 1983.
Nancy C. Andreasen, Methods for Assessing Positive and Negative Symptoms, Department of Psychiatry, University of Iowa College of Medicine, 1990, vo. 24, pp. 73-88.

* cited by examiner

*Primary Examiner*—Jennifer M Kim
(74) *Attorney, Agent, or Firm*—Roylance, Abrams, Berdo & Goodman, L.L.P.

(57) ABSTRACT

Use of neboglamine, (S)-4-amino-N-(4,4-dimethylcyclohexyl)glutamic acid (CR 2249) (CAS Registry Number 163000-63-3), of the racemate thereof or of a pharmaceutically acceptable salt thereof for the preparation of a medicament for the treatment of schizophrenia.

9 Claims, No Drawings

USE OF NEBOGLAMINE (CR 2249) AS AN ANTIPSYCHOTIC AND NEUROPROTECTIVE

FIELD OF THE INVENTION

The present invention relates to a novel therapeutic use for (S)-4-amino-N-(4,4-dimethylcyclohexyl)glutamic acid (CR 2249-neboglamine) (CAS Registry Number 163000-63-3), of the pharmaceutically acceptable salts thereof and of the main metabolite thereof, 4,4-dimethylcyclohexylamine (CR 2863), in the treatment of schizophrenia with predominant negative symptomatology, of type II bipolar disorders (hypomania with major depression) and in cyclothymic disorders (numerous episodes of hypomania and minor depression).

BACKGROUND OF THE INVENTION

Schizophrenia is a psychiatric condition characterised by positive symptoms, for example hallucinations, delusions, disturbances of thought, paranoia [Andreson, Mod. Probl. Pharmacopsychiatry 24, 73-88 (1990); Peralta et al., Br. J. Psychiatry 161, 335-343 (1992)], negative symptoms, for example apathy which primarily manifests as emotional and motivational deficits and deficits in social interactions, cognitive deficit together with depression.

This complex scheme of symptoms which is observed in schizophrenic patients suggests the existence of dysfunctions at various levels in the brain of these individuals and it is thus difficult to hypothesise that malfunctioning of a single neurotransmitter system could explain the complex pathological picture of the disease.

The until recently accepted hypothesis suggested hyperactivity of the dopaminergic system as the primary cause of the clinical manifestations of schizophrenia. This hypothesis was largely derived from the observation that amphetamine brings about positive symptoms which resemble those present in paranoid patients; this symptomatology is brought about by increased dopaminergic neurotransmission in the central nervous system (CNS) (Sayed et al., Psychopharmacol. Bull. 19, 283-288 (1983)].

However, many schizophrenic patients and in particular those exhibiting predominantly negative symptoms do not respond adequately to treatment with dopamine antagonist drugs, so demonstrating that the dopaminergic model can only provide a partial explanation of the complexity of the disease.

Functional anatomical studies have revealed morphometric changes in the cerebral cortex of schizophrenic individuals, these changes probably arising from modified cortical development. Glutamate is the primary neurotransmitter at this level and it is thus probable that dysfunction of the glutamatergic pathways may well play an important part in schizophrenia as it does in bipolar disorders. The dopaminergic and glutamatergic hypotheses are not mutually exclusive because there are major functional interactions between these two neurotransmitter systems.

One limitation of preclinical studies into novel molecules with potential antipsychotic activity is the limited availability of animal models capable of meaningfully reproducing a complex pathological picture such as that presented by schizophrenia. Despite this, there are models which can sufficiently effectively reproduce the symptoms of such disease with the aim of assessing the pharmacological activity of the potential candidate drug in specific functional changes.

On the basis of published preclinical data, the compound neboglamine (CR 2249) has shown that it possesses considerable modulating properties for the (strychnine-insensitive) glycine site coupled to the NMDA receptor complex [Lanza et al., Neuropharmacology 36, 1057-64 (1997)] together with interesting properties promoting memory and learning in various animal models [Garofalo et al. J. Pharm. Pharmacol. 48, 1290-97 (1996)].

The facilitatory activity exerted by neboglamine at the level of the NMDA receptor complex should be of therapeutic utility under conditions involving glutamatergic hypofunctionality, which, as explained above, may contribute to the negative symptomatological picture of schizophrenia.

SUMMARY OF THE INVENTION

Phenylcyclidine (PCP) induced psychosis is one model which better reflects the pathophysiology of the disease. In fact, both in experimental animals and in humans, PCP induces behavioural effects which exhibit considerable similarities with the symptoms of schizophrenia [Jentsch et al., Neuropsychopharmacology 20, 201-225 (1999)]. Accordingly, in humans, chronic administration of PCP (as may occur, for example, in drug addicts) brings about persistent neurobiological changes which are manifested with both positive and negative typologies, and mimic those present in schizophrenic patients.

Thus, neboglamine and the main metabolite thereof CR 2863 have been evaluated in experimental animal models in which PCP was used and which are recognised as being predictive for the evaluation of antipsychotic drugs. Such models in fact reproduce both glutamatergic hypofunctionality and hyperactivity of the dopaminergic system (hyperactivity and stereotype behaviour) with a psychotomimetic state which greatly resembles schizophrenia, unlike amphetamine-induced models which only bring about positive type psychoses.

The first model used was the study of PCP-induced inhibition of the acoustic prestimulus (PPI) in the rat.

Principle of the Method

The extent of the startle reflex response to an acoustic stimulus is reduced if it is preceded by a weak stimulus which, by itself, does not bring about a significant startle response. This phenomenon is known as "pre-pulse inhibition" (PPI). This PPI response is present both in many animal species and in humans, while it has on the contrary been reported that schizophrenic patients generally exhibit a PPI deficit. Such a deficit may be reproduced experimentally with drugs which induce psychotic phenomena, such dopamine agonists and NMDA antagonists.

The method is based on that reported by Swerdlow et al. [J. Pharmacol. Exp. Ther. 256 530-536 (1991)] with slight modifications. An acrylic cylinder is used which is equipped with a piezoelectric sensor mounted under the cylinder which detects and transduces movements of the cylinder. A background noise of 60 dB is provided and subsequently two acoustic stimuli separated by 500 ms, the first of which is 20 dB above the background noise, while the second (startle stimulus) is 120 dB for a duration of 40 ms. The session of 30 trials at 30 second intervals with an overall duration of approx. 15 minutes involved subjecting the animal randomly to a startle stimulus either isolated or preceded by the low intensity stimulus. PPI was calculated as a percentage reduction in the level of startle in the presence of the prestimulus compared to that without the acoustic prestimulus. Rats weighing approx. 250 g were used, which were treated intraperitoneally (i.p.) with the products under investigation 15 minutes prior to subcutaneous (s.c.) administration of 3 mg/kg of PCP and 30 minutes before the beginning of the experiment. The results obtained are shown in Table 1 below.

TABLE 1

Reversion of PCP-induced inhibition of the
acoustic prestimulus (PPI) in the rat

| PPI | (% inhibition)[1] | % inhibition by PCP[2] |
|---|---|---|
| Control | 55% | — |
| PCP | 20% | — |
| PCP + N (1)[3] | 27% | 20.0 |
| PCP + N (3)[3] | 40* | 57.1 |
| PCP + N (10)[3] | 48* | 80.0 |
| PCP + CR2863 (10)[3] | 38* | 51.4 |

Note N = neboglamine
[1]: The results relate to 10 animals per group; * P < 0.05 (ANOVA vs PCP only group)
[2]: Perdcentage inhibition iss calculated with the formula:
$$\frac{[(N + PCP) - PCP]}{CONTROL - PCP} \times 100$$

[3]: The numbers in brackets are the doses of drug in mg/kg i.p.

Analysis of the PPI data of the animals pretreated with the drugs under investigation shows how neboglamine dose-dependently inhibits the blocking of PPI by PCP. This inhibition is already significant at a dose of 3 mg/kg (i.p.). The metabolite CR 2863 proves to be approx. 3 times less active than the "parent" in this experimental model.

An animal model of depression (which may be considered as a negative symptom of schizophrenia) was then used to study the activity of neboglamine on the PCP-induced depressive effects in the mouse using the swimming test according to Porsolt et al. [Arch. Int. Pharmadyn. 229, 327-336 (1977)].

Method

The test involves inducing a state of depression in the animal, which is forced to swim in a glass cylinder from which it cannot escape. The state of depression was accentuated by 14 days' pre-treatment with a daily 10 mg/kg (s.c.) injection of PCP. On the 15th day, the animals were additionally pretreated (i.p.) with physiological solution or neboglamine 30 minutes before the beginning of the test. The duration of immobility (sign of depression) in seconds was evaluated during the experiment of an overall duration of 360 seconds. The results obtained in this manner, calculated between the 3rd and 6th minute of the experiment, i.e. for a period of 240 seconds, are shown in Table 2.

TABLE 2

Reversion of PCP-induced depression in the mouse
swimming test

| Control group | Immobility in seconds | % effect[2] vs PCP |
|---|---|---|
| Control | 48 | — |
| PCP | 130 | — |
| Neboglamine (3) + PCP | 84 | 56.0 |
| Neboglamine (N) (10) + PCP | 58[91)] | 87.8 |

[1]: P < 0.01 vs PCP only group (n = 10 animals/group)
[2]: Percentage inhibition iss calculated with the formula:
$$\frac{[PCP - (N + PCP)]}{(PCP - CONTROL)} \times 100$$

It may be inferred from the data shown in Table 2 how 2 weeks' chronic treatment with PCP at a dose of 3 mg/kg brings about a behavioural change in the animals in an experiment which is considered as a possible model of the negative symptomatology of schizophrenia. The duration of immobility of the PCP-treated group in fact increased by approx. 3 times relative to the untreated control group In the dose range from 3-10 mg/kg, neboglamine successfully inhibits this effect, which becomes statistically significant at a dose of 10 mg/kg, with virtually complete inhibition (87.8%) of the depressive effect.

Neboglamine's ability to reverse the effect of PCP at a neuronal level was also evaluated in an in vitro test carried out on slices of rat frontal cortex.

The method involved preparing 0.4 mm thick cortical slices, incubating them for 20 minutes with $^3$H-dopamine in physiological solution in the presence of 0.1 μM 6-nitroquipazine and 0.1 μM nisoxetine (selective serotonin and noradrenaline reuptake inhibitors), aerated with 95% $O_2$+5% $CO_2$ at 37° C., which, after appropriate washing with artificial cerebrospinal fluid (aCSF), were superperfused for 30 minutes with aCFS at a rate of 1 ml/minute to equilibrate the system. Then, PCP and neboglamine were added at the stated concentrations to the perfusion liquid for the entire duration of the experiment, while, after 45 minutes, NMDA (100 μM) stimulation was provided for 5 minutes. Another four 5 minute fractions of eluate were then collected and their radioactivity determined.

The effect of the drugs was evaluated by calculating the ratio between the percentage radioactivity present in the effluent fraction corresponding to the maximum effect and that in the first effluent fraction collected. The results obtained are shown in Table 3 below.

TABLE 3

Effect of neboglamine in inhibiting PCP-induced
blocking on the release of tritiated dopamine
brought about by NMDA in slices off rat prefrontal
cortex

| | Groupss | % increase in NMDA-evoked 3H-dopamine release | % inhibitory effect of PCP[3] |
|---|---|---|---|
| I: | Control (NMDA) (100)[1] | 120 | — |
| II: | NMDA + PCP (0.1) | 64 | — |
| III: | NMDA + PCP + neboglamine (10) | 84[2] | 35.7 |
| IV: | NMDA + PCP + neboglamine (30) | 110[2] | 82.1 |

[1]: All concentrations are μM;
[2]: P < 0.05 (ANOVA) (n = 9 × group)
[3]: Percentage inhibition was calculated with the formula:
$$\frac{[III(IV) - II]}{(I - II)} \times 100$$

It may be inferred from the data shown in Table 3 how neboglamine powerfully and dose-dependently prevents PCP-induced blocking of NMDA-evoked dopamine release. This inhibition was deemed significant from a dose of as low as 10 μM. It should furthermore be noted that, at both the concentrations tested, neboglamine has no effect on basal dopamine release.

Neuroprotection Experiments

It was decided to investigate whether neboglamine and the main metabolite thereof (CR 2863) could additionally exhibit neuroprotective activity: such properties could in fact prove to be extremely useful because a considerable sub-population of schizophrenic patients suffers from progressive structural degeneration of the brain (neurodegeneration), the prevention of which is essential if cognitive function is to be maintained or restored.

It was accordingly decided to investigate the possible neuroprotective effects of neboglamine and CR 2863 on a model of hippocampal ischaemia brought about in the gerbil by bilateral occlusion of the carotid arteries.

In brief, halothane-anaesthetised animals are subjected to bilateral occlusion of the carotid arteries for 5 minutes. After 7 days, the animals are sacrificed, the brain is removed, deep frozen and 10 μm sections from the hippocampal area are prepared which are stained with cresyl violet. A quantitative determination (in mm$^2$) of the area occupied by CHI pyramidal neurons is then performed by means of an image analyser. The type of hippocampal neurodegeneration arising from this model of ischaemia involves a significant reduction in the area of the neuronal nuclei. The drugs were administered intraperitoneally (i.p.) 1 h before the ischaemia. The results obtained in this manner are shown in Tables 4 and 5 below.

TABLE 4

Ischaemia induced in the gerbil by bilateral occlusion of the carotid arteries: protective effect of neboglamine

| Substances | Dose mg/kg | area (mm$^2$) | % protection | % mortality |
|---|---|---|---|---|
| Controls (Sham) | — | 25.22 ± 2.13 | — | 0 |
| Ischaemia | — | 9.05 ± 5.98* | — | 50 |
| CR 2249 | 12.5 | 8.42 ± 4.46* | 0 | 50 |
| CR 2249 | 25 | 16.47 ± 5.54*+ | 45.9 | 25 |
| CR 2249 | 50 | 20.48 ± 5.3+ | 70.7 | 0 |

The data are means ± SD.
*P < 0.05 vs sham animals.
+P < 0.05 vs ischaemic animals

TABLE 5

Ischaemia induced in the gerbil by bilateral occlusion of the carotid arteries: protective effect of CR 2863

| Substances | Dose mg/kg | area (mm2) | % protection | % mortality |
|---|---|---|---|---|
| Controls (Sham) | — | 22.39 ± 1.15 | — | 0 |
| Ischaemia | — | 5.55 ± 3.1* | — | 28.57 |
| CR 2863 | 4 | 9.74 ± 0.9*+ | 24.88 | 11.11 |
| CR 2863 | 8 | 12.16 ± 5.49* | 39.25 | 5.88 |
| CR 2863 | 16 | 15.23 ± 5.49*+ | 57.82 | 0 |

The data are means ± SD.
*P < 0.05 vs sham animals.
+P < 0.05 vs ischaemic animals It can be seen from the data shown in Tables 4 and 5 how neboglamine provides dose-dependent protection from neuronal degeneration. Indeed, while ischaemia produces a mortality of 50% in the control animals, neboglamine at the higher dose completely eliminates any mortality. Furthermore, in this model, the metabolite CR 2863 proves to be still more active than the "parent", since complete protection against mortality is achieved at a dose of as low as 16 mg. These results would suggest that the neuroprotective effect exhibited by neboglamine is principally due to its main metabolite CR 2863.

Pharmaceutical formulations for the use of the compounds according to the invention may be prepared using conventional methods. The formulations include those suitable for oral use such as capsules, tablets, suspensions, emulsions, solutions; sterile solutions for parenteral use (including subcutaneous, intramuscular, intravenous), or preparations for topical or rectal use or other forms suitable for achieving the desired therapeutic effect, for example solid formulations for oral use with delayed action which allows slow release of the active ingredient over time.

Substances commonly used in the pharmaceutical sector such as excipients, binders, disintegrants, substances capable of promoting transdermal absorption may be used together with the active ingredient in the pharmaceutical formulation.

Neboglamine compounds and the compound thereof, CR 2863, may accordingly be used as such or as pharmaceutically acceptable salts. In the case of neboglamine, the sodium or potassium salt or the hydrochloride is preferred, while the hydrochloride is preferred in the case of CR 2863.

The effective therapeutic quantity of neboglamine to be used for the treatment of schizophrenia should be between 10 and 600 mg of active ingredient per day, preferably from 30 to 300 mg, depending on the specific condition of the treated patient, on the individual response to treatment, the age and weight of the patient.

The following Examples are intended to illustrate better the present invention in a purely exemplary, non-limiting manner.

EXAMPLE 1

Composition of Neboglamine Capsules

| Snap Fit hard gelatin capsules, Size 1 | |
|---|---|
| Neboglamine | 100 mg |
| Pregelatinised maize starch | 228 mg |
| USP talcum | 2 mg |

EXAMPLE 2

Composition of an Oral Solution (Syrup) of Neboglamine (Per 100 ml of Syrup)

| Neboglamine | 1 g |
|---|---|
| Sodium hydroxide pellets | 0.15 g |
| Essential oil | 0.05 g |
| Sorbitol, 70% | 65 g |
| Ethyl alcohol, 95% | 5 g |
| Distilled water to make up to | 100 ml |

EXAMPLE 3

Composition of a Sterile Vial of Neboglamine for Parenteral Use

| Neboglamine | 50 mg |
|---|---|
| Sodium hydroxide pellets | 7.5 mg |
| Pyrogen-free physiological solution to make up to | 3 ml |

The invention claimed is:

1. A method for treating schizophrenia in a patient by administering to said patient in need thereof an effective amount of an active ingredient selected from the group consisting of (s)-4-amino-N-(4,4-dimethylcyclohexyl) glutamic acid; a racemate containing (s)-4-amino-N-(4,4-dimethylcyclohexyl) glutamic acid; 4,4-dimethylcyclohexylamine; and a pharmaceutically acceptable salt thereof.

2. The method of claim 1, further comprising administering to said patient having symptoms of type II bipolar (manic depressive) disorders the active ingredient in an effective amount for the therapeutic treatment of type II bipolar (manic-depressive) disorders.

3. The method of claim 1, further comprising administering to said patient having symptoms of cyclothymic disorders the active ingredient in an effective amount for the therapeutic treatment of cyclothymic disorders.

4. The method of claim 1, further comprising administering to said patient having symptoms of progressive structural degeneration of the brain the active ingredient in an effective amount for the therapeutic neuroprotective treatment of pathological conditions characterized by progressive structural degeneration of the brain.

5. The method of claim 1, wherein said active ingredient comprises 4,4-dimethylcyclohexylamine (CR 2863) or of a pharmaceutically acceptable salt thereof and where said method comprises administering said active ingredient in an amount effective for the treatment of symptoms of depression by said patient.

6. The method of claim 1, wherein said active ingredient comprises 4,4-dimethylcyclohexylamine (CR 2863) or of a pharmaceutically acceptable salt thereof and where said method comprises administering said active ingredient in an amount effective for the treatment of schizophrenia.

7. A method for treatment of symptoms of type II bipolar (manic-depressive) disorder in a patient suffering from schizophrenia comprising the step of administering to said patient in need thereof a 4,4-dimethylcyclohexylamine or a pharmaceutically acceptable salt thereof in an amount effective to treat type II bipolar (manic-depressive) disorder.

8. The method of claim 7, comprising administering to said patient having symptoms of progressive structural degeneration of the brain said 4,4-dimethylcyclohexylamine in an amount effective for therapeutic neuroprotective treatment of pathological conditions characterized by progressive structural degeneration of the brain.

9. A method for treating negative symptoms of schizophrenia in a patient by administering to said patient an effective amount of 4,4-dimethylcyclohexylamine and a pharmaceutically acceptable salt thereof.

* * * * *